(12) United States Patent
Pichler-Wilhelm et al.

(10) Patent No.: US 10,434,224 B2
(45) Date of Patent: Oct. 8, 2019

(54) MEDICAL GLASS ELEMENT

(71) Applicant: SCHOTT AG, Mainz (DE)

(72) Inventors: Sabine Pichler-Wilhelm, Landshut (DE); Oliwia Makarewicz, Jena (DE); Christian Lautenschläger, Cambridge (GB); Mareike Klinger-Strobel, Jena (DE); Andreas Stallmach, Eckartsberga (DE); Mathias W. R. Pletz, Jena (DE)

(73) Assignee: SCHOTT AG, Mainz (DE)

( * ) Notice: Subject to any disclaimer, the term of this patent is extended or adjusted under 35 U.S.C. 154(b) by 34 days.

(21) Appl. No.: 15/862,840

(22) Filed: Jan. 5, 2018

(65) Prior Publication Data

US 2018/0193533 A1 Jul. 12, 2018

Related U.S. Application Data

(63) Continuation of application No. 15/272,928, filed on Sep. 22, 2016, now Pat. No. 9,956,322.

(30) Foreign Application Priority Data

Sep. 22, 2015 (DE) .................. 10 2015 115 958

(51) Int. Cl.
*A61L 31/08* (2006.01)
*A61L 29/10* (2006.01)
(Continued)

(52) U.S. Cl.
CPC ............ *A61L 31/088* (2013.01); *A61F 2/00* (2013.01); *A61L 27/306* (2013.01); *A61L 27/54* (2013.01); *A61L 29/106* (2013.01); *A61L 29/14* (2013.01); *A61L 29/16* (2013.01); *A61L 31/14* (2013.01); *A61L 31/16* (2013.01); *C03C 3/093* (2013.01);
(Continued)

(58) Field of Classification Search
None
See application file for complete search history.

(56) References Cited

U.S. PATENT DOCUMENTS

2007/0122356 A1 5/2007 Kessler et al.
2007/0172661 A1 7/2007 Fechner
(Continued)

FOREIGN PATENT DOCUMENTS

DE 19532800 A1 2/1997
DE 10120475 10/2002
(Continued)

*Primary Examiner* — Carlos A Azpuru
*Assistant Examiner* — Casey S Hagopian
(74) *Attorney, Agent, or Firm* — Ohlandt, Greeley, Ruggiero & Perle, L.L.P.

(57) ABSTRACT

A material that is less populated by biofilms than known materials and is well tolerated by the body is provided. The material is an element introducible into or attachable on a human or animal body and includes a glass and/or glass ceramic and/or ceramic material at least in some areas thereof, which inhibits the formation of biofilms and/or on which human or animal cells grow if the element is introduced into the human or animal body or attached thereto, wherein the glass and/or glass ceramic material comprises at least: $SiO_2$ in a range from 60 to 75 wt % and ZnO in a range from 1 to 7 wt %.

16 Claims, 10 Drawing Sheets
(1 of 10 Drawing Sheet(s) Filed in Color)

(51) Int. Cl.
 *A61L 29/14* (2006.01)
 *A61L 31/14* (2006.01)
 *C03C 3/093* (2006.01)
 *C03C 4/00* (2006.01)
 *C03C 10/00* (2006.01)
 *A61F 2/00* (2006.01)
 *C03C 8/04* (2006.01)
 *A61L 27/30* (2006.01)
 *A61L 27/54* (2006.01)
 *A61L 29/16* (2006.01)
 *A61L 31/16* (2006.01)

(52) U.S. Cl.
 CPC .............. *C03C 4/0007* (2013.01); *C03C 8/04* (2013.01); *C03C 10/0018* (2013.01); *A61L 2300/404* (2013.01); *A61L 2420/06* (2013.01); *C03C 2204/02* (2013.01)

(56) References Cited

U.S. PATENT DOCUMENTS

2007/0225424 A1 9/2007 Schulz et al.
2011/0275031 A1* 11/2011 Jana .................. A61C 13/0006
 433/172
2012/0219792 A1 8/2012 Yamamoto

FOREIGN PATENT DOCUMENTS

DE 102004023732 12/2005
DE 102004026432 A1 12/2005
DE 102006014095 A1 9/2007
WO 2004076369 9/2004

* cited by examiner

|  | Soda-Lime | Boro33 | AS87 | D263T | D263T eco |
|---|---|---|---|---|---|
| MSSA | | | | | |
| Enterococcus faecalis | | | | | |
| Enterococcus faecium | | | | | |
| Escherichia coli | | | | | |
| Klebsiella pneumonia | | | | | |
| Pseudomonas aeruginosa | | | | | |
| Proteus mirabilis | | | | | |
| Staphylococcus epidermidis | | | | | |

Fig. 8

MEDICAL GLASS ELEMENT

CROSS REFERENCE TO RELATED APPLICATION

This application is a continuation of U.S. Ser. No. 15/272,928, filed Sep. 23, 2016, which claims benefit under 35 U.S.C. § 119(a) of German Patent Application No. DE 10 2015 115 958.9 filed Sep. 22, 2015, the entire contents of which are incorporated herein by reference.

BACKGROUND

1. Field of the Invention

The invention relates to an element introducible into or attachable on a human or animal body, comprising a glass and/or glass ceramic and/or ceramic material at least in some areas thereof. Furthermore, the invention relates to a glass and/or glass ceramic and/or ceramic material for such an element, and to the use of a corresponding glass and/or glass ceramic and/or ceramic material for producing an element introducible into or attachable on a human or animal body.

2. Description of Related Art

Biofilms are complex communities of microorganisms in nutrient-rich aqueous systems. Their formation is related to the adhesion and colonization of surfaces through the production of extracellular sticky polymers. The formation of biofilms is also referred to as micro fouling and constitutes the first step of macro fouling, which means the colonization or development of macroscopic fouling organisms.

In the medical field, components that are permanently present in or on the body, such as catheters, prostheses, artificial heart valves, implants, pacemakers, and the like are highly susceptible to micro fouling. This is accompanied by the risk of biofilm-associated diseases and infections.

Biofilms are largely insensitive to environmental factors such as ultraviolet radiation and to chemical treatments with, e.g., detergents, i.e. surface active components. Moreover, biofilms hardly respond to antibiotics and exhibit protection against the immune system of the host. It is estimated that *S. aureus* and *S. epidermidis* are causing about 40% to 50% of the infections on artificial heart valves and between about 50% and 70% of the biofilm infections on catheters.

SUMMARY

An object of the invention is to provide a material that is less populated by biofilms than known materials for elements attachable on the human or animal body or introducible into the body.

Another object of the invention is to provide a material which moreover is well tolerated by the body.

These objects are achieved in a manner very surprisingly for a person skilled in the art by an element introducible into or attachable on a human or animal body, which comprises a glass and/or glass ceramic and/or ceramic material at least in some areas thereof, which inhibits the formation of biofilms and/or on which human or animal cells grow if the element is introduced into the human or animal body or attached thereto, wherein the glass and/or glass ceramic and/or ceramic material comprises at least: $SiO_2$ in a range from 60 to 75 wt %, and ZnO in a range from 1 to 7 wt %.

It is advantageous if the element inhibits the formation of biofilms. Alternatively it is possible and also advantageous if human or animal cells grow on the element when it is introduced in the human or animal body or attached thereto. It is particularly advantageous if the element both inhibits the formation of biofilms and human or animal cells grow on the element when it is introduced in the human or animal body or attached thereto. All these features are within the scope of the invention.

The inventors have found that, surprisingly, the glass or glass ceramic or ceramic material inhibits the formation of biofilms on the one hand, and on the other, advantageously, human or animal cells grow on the glass or glass ceramic or ceramic material when the element is introduced into the human or animal body or attached thereon. According to the findings of the inventors, eukaryotic and prokaryotic cells show an opposite reaction to the glass or glass ceramic or ceramic material with the composition according to the invention. This is exploited by the invention by using the glass and the glass ceramic and the ceramic for components which come in contact with or in particular are even introduced into the human or animal body and for which high hygiene requirements are existing. The same material according to the invention allows inhibition of an accumulation of biofilms on the one hand and preferably also promotes compatibility and even ingrowth in or growth of body cells thereon. It has been found that eukaryotic cells are not affected in terms of their growth and normal cell division (i.e. no special cell adhesion for eukaryotic cells). Thus, the materials of the invention are not cytotoxic.

In the context of the present application the indication "wt %" is based on the total amount of oxides, that is to say the given amounts of the constituents of the glass and/or glass ceramic and/or ceramic materials are specified in "wt % on oxide basis".

"Element" refers to a body that may consist of solid material, but may as well be formed with at least one cavity. The shaping of the inventive element is freely selectable by the skilled person within the manufacturing options for elements made of glass and/or glass ceramic and/or ceramic material, depending on the application of the element. Moreover, within the scope of the invention, the element may as well be provided in the form of bulk material, for example as a powder, or as an additive for suspensions.

The further constituent components or oxides of the glass or glass ceramic or ceramic material will be selected for the relevant application by a person skilled in the art based on his expertise and also in view of the later application, connection with other materials (e.g. metals or ceramics), the type of melting and/or further processing. Moreover, refining agents may be added.

"Growth of human or animal cells thereon" means that the glass and/or glass ceramic and/or ceramic material is not cytotoxic to these cells and is compatible with blood (hemocompatible). The interaction between the surface of the glass and/or glass ceramic and/or ceramic material with erythrocytes as the main components of blood and one of the first contact partners after systemic administration were determined by hemolysis and erythrocyte aggregation.

Cytotoxicity was determined by the inventors with respect to muscle cells, Caco2 cells, and L929 mouse fibroblasts. To this end, the glass and/or glass ceramic material with the respective cells was cultured in DMEM (Life Technologies) for 48 hours. The experiments were performed at 37° C. under an atmosphere of +5% $CO_2$. This corresponds to standardized tests for cytotoxicity to eukaryotic cells. Cytotoxicity was evaluated on the basis of cell growth and cell morphology. Morphological changes and cell damage were determined qualitatively from digital photographs by a light phase contrast microscope.

For determining hemolysis and erythrocyte aggregation, human red blood cells were incubated on the relevant glass and/or glass ceramic material for two hours at 37° C. The red blood cells were obtained from blood which was collected in heparinized tubes. The suspensions of red blood cells were then used within 24 hours.

The release of hemoglobin was used to quantify a damaging effect of the glass and/or glass ceramic material on the erythrocyte membrane. The treatment of the red blood cells with PBS buffer and with a solution of 1% Triton X-100 resulted in 0% and 100% hemolysis, respectively. For determining hemolysis, hemoglobin release was determined by spectroscopic analysis of the supernatant at 544 nm. A release from 0 to 2% of the total release was classified non-hemolytic, a release in the range between 2% and 5% of the total release was classified slightly hemolytic, and a release of more than 5% of the total release was classified as hemolytic, according to the ASTM F756-08 standard.

For determining erythrocyte aggregation, micrographs were evaluated by classification into three levels. In level 1, the red blood cells remained discretely distributed in the suspension, without detectable aggregation. In level 2, moderate aggregation can be seen, with rouleau formation, but the majority of erythrocytes is discrete. This was found in microscopic observations of known methodology (see Bauer et al., Macromol. Biosci. 2012, 12, 986-998). In level 3, nearly all red blood cells are aggregated to form clusters. For determining level 1, the erythrocytes were treated with PBS as a negative control. Positive controls were treated with 30 mg/mL 25 kDa branched polyethyleneimine and classified as level 3.

The term "inhibiting the formation of biofilms" means that compared to glasses and/or glass ceramics that are usually employed as a substrate for microbial colonization, such as borosilicate glass, e.g. applicant's "Borofloat 33", or soda-lime glass (Paul Marienfeld GmbH), a smaller surface area is covered by biofilm if the glass of the invention and/or the glass ceramic of the invention is used.

The coverage by biofilm can be determined by visualization, for example. The inventors performed appropriate experiments using a LSM510 confocal laser scanning microscope by scanning a surface area of 100 μm by 100 μm (microns) on the green channel (480/500 nm) and the red channel (490/635 nm). A 40×10 water immersion objective was used for this purpose. The images of the biofilms were visualized using ZEN 9.0 software (Carl Zeiss Microscopy GmbH).

The area covered by biofilm within an image is calculated based on a separation of pixels from the background according to the brightness thereof. A 16 bit image is divided into 256 gray levels (0=black; 255=white). By applying a threshold according to Otsu, all covered areas can be reliably identified. The area covered by biofilm was calculated with respect to the total number of pixels of an image using ImageJ 1.43u software.

A glass ceramic material usually is understood to be a material which is made from the same starting materials as a glass, but for which during processing the glass is transferred into a partially crystalline and partially amorphous, i.e. glassy state before, during, or after molding, for example by selective temperature control. Even complete devitrification is possible and within the scope of the invention.

"Glass ceramic material" usually refers to a material in which both crystalline phases and amorphous phase, i.e. glass phases, coexist. Zones with crystalline phases may in particular be interconnected by glass phases. A glass ceramic can be considered a partially crystallized glass so to speak, in which the degree of crystallization may widely vary, even approaching 100%.

Also encompassed by the invention is the case where the material is a ceramic, i.e. it is fully crystallized. Crystallization may in particular be achieved by process control during the manufacturing of the material and/or further processing thereof, in particular by cooling and/or heating.

The crystalline phases may usually be embedded in the glass phase.

In an advantageous embodiment of the invention, the glass and/or glass ceramic and/or ceramic material comprises at least the following components:

$SiO_2$ in a range from 60 to 75 wt %
$R_2O$ in a range from 5 to 20 wt %
RO in a range from 0 to 10 wt %
$Al_2O_3$ in a range from 1 to 6 wt %
$B_2O_3$ in a range from 0 to 10 wt %
$TiO_2$ in a range from 0 to 8 wt %
ZnO 1 to 7 wt %
FeO 0 to 5 wt %, wherein $R_2O$ is an oxide or a combination of oxides selected from the group comprising $Li_2O$, $Na_2O$, and $K_2O$, and wherein RO is an oxide or a combination of oxides selected from the group comprising MgO and/or CaO and/or BaO and/or SrO. The total amount of $R_2O$ and/or RO may comprise one or more oxides of the relevant specified group in any combination of the oxides.

Iron oxide is added to the glass for achieving fusion using IR lamps or lasers performing at a wavelength of 1060 nm. Absorption should preferably be between 2 and 20%. This is the case with FeO contents from 2.7 to 5%. The thinner the wall thickness of the glass to be fused, the stronger should be the absorption and accordingly the higher should be the FeO content. If during melting of the glass the iron is added in the form of $Fe_2O_3$, it must be ensured by appropriate melting control that a sufficient amount of Fe(III) is reduced to Fe(II) in order to obtain the specified FeO contents in the glass. Iron oxide may be present in the glass in different oxidation states and is specified in the form of FeO herein. A person skilled in the art will know how to convert this into proportions of Fe(III) and $Fe_2O_3$, if he wishes to specify the proportion of $Fe_2O_3$, for instance for synthesis purposes.

In particular it has been found advantageous for the glass and/or glass ceramic and/or ceramic material to comprise:

$SiO_2$ in a range from 60 to 70 wt %
$R_2O$ in a range from 5 to 20 wt %
RO in a range from 0 to 10 wt %
$Al_2O_3$ in a range from 1 to 5 wt %
$B_2O_3$ in a range from 0 to 10 wt %
$TiO_2$ in a range from 0 to 8 wt %
ZnO in a range from 1 to 7 wt %
FeO in a range from 0 to 5 wt %, with
$Na_2O$ in a range from 2 to 10 wt %, and/or
$K_2O$ in a range from 3.5 to 10 wt %,
wherein $R_2O$ is an oxide or a combination of oxides selected from the group comprising $Li_2O$, $Na_2O$, and $K_2O$, and wherein RO is an oxide or a combination of oxides selected from the group comprising MgO and/or CaO and/or BaO and/or SrO.

It is of particular advantage if the glass and/or glass ceramic and/or ceramic material is free of CuO, except for impurities. Impurities may usually be present in a content of up to 0.3%. This means that the CuO content is advantageously from 0 to 0.3%, most advantageously 0%.

The described glass and/or glass ceramic and/or ceramic material is moreover particularly suitable for producing hermetic feedthroughs, especially with titanium and/or several titanium alloys. In such a feedthrough, a functional element is usually held in a feedthrough opening of a carrier member by an insulating element thereby hermetically sealing the feedthrough opening. The carrier member may in particular be a casing and/or a casing part, here in particular of a casing or casing component made of titanium or titanium alloys, and the functional element may in particular be an electrical conductor. Other functional elements, such as e.g. optical fibers, waveguides, hollow waveguides, tubes, capillaries, and the like are of course also encompassed by the invention. The insulating element is made of the described glass and/or glass ceramic and/or ceramic material and for example has the shape of a plug.

The suitability of the glass and/or glass ceramic and/or ceramic material in particular for producing feedthroughs with titanium and/or titanium alloys is due to the chemical compatibility with these metals and/or the thermal expansion coefficients thereof. Particularly advantageously the coefficient of thermal expansion of the glass and/or glass ceramic and/or ceramic material is lower than that of titanium and/or the titanium alloy in question, so that a so-called compression feedthrough may be produced.

In such a case, when fusing the functional element to the carrier member using the insulating material, the carrier member will shrink onto the insulating element so that at least at room temperature the carrier member will exert a compressive stress to the insulating element. In this manner the extraction force which is the force that is needed to urge the insulating element out of the carrier member can in particular be significantly increased, and/or a reliable and permanently hermetically sealed feedthrough can be provided.

Particularly good results have been obtained with a glass and/or glass ceramic and/or ceramic material comprising:

$SiO_2$ in a range from 62 to 66 wt %
$Al_2O_3$ in a range from 3.8 to 4.5 wt %
$B_2O_3$ in a range from 0 to 10 wt %
$TiO_2$ in a range from 3.5 to 4.5 wt %
$ZnO$ in a range from 5 to 7 wt %
$FeO$ in a range from 0.001 to 0.005 wt %
$Na_2O$ in a range from 5.9 to 6.5 wt %, and
$K_2O$ in a range from 8.3 to 9.1 wt %, where
$SeO_2$ may be present in a content of up to 0.04 wt %.

In particular, the glass and/or glass ceramic material may comprise a content of Ag of less than 0.3 wt % and/or a content of $P_2O_5$ of less than 0.5 wt % and/or a content of F of less than 1 wt %. Particularly advantageously the proportion of Ag and/or $P_2O_5$ is selected so as to be as low as possible, especially if the glass and/or glass ceramic material is free of these substances, except for impurities at the most. In particular, this includes the content of 0%. This lower limit also applies to $F_2$. However, it may as well be advantageous if the glass and/or glass ceramic material includes a certain small percentage of $F_2$. Therefore, according to one advantageous embodiment a content of $F_2$ of more than 0 wt % up to less than 1 wt % is contemplated.

According to one advantageous embodiment of the invention it is contemplated that for applications in or on the body the element comprises at least one casing or constitutes a casing which is designed for accommodating active and/or passive electronic components, and in this case the casing consists of the glass and/or glass ceramic material at least in sections thereof, and/or the casing has at least one coating made of the glass and/or glass ceramic material at least in areas thereof. It is likewise possible that additionally or alternatively the casing is provided with means for delivering active substances, such as a membrane and/or a valve, and the like. In this way, active substances, especially medicines, can be delivered in the body and advantageously at a predefined point, for example directly into the bloodstream.

In one embodiment, the element of the invention thus comprises or constitutes a casing for electronic components which is made of the glass at least in sections thereof or on which the glass is applied as a layer at least in areas thereof.

In a particularly simple implementation, the casing comprises a tube made of the glass and/or glass ceramic material. More particularly, the element is a glass tube that is in particular sealed on one or both ends thereof. The element may furthermore be in the form of a casing for electronic devices such as transponders or entire defibrillators, pacemakers, or labs-on-chip, or may be formed as a contact lens, for example.

Furthermore within the scope of the invention, the element may be an implant, a hermetically sealed feedthrough, a vascular support, in particular a stent, or a catheter or a similar component that can be introduced into the human or animal body.

The invention also provides a glass and/or glass ceramic and/or ceramic material for use as an element inhibiting the formation of biofilms and/or as an antibacterial element, and/or as a region of an element inhibiting the formation of biofilms and/or as an antibacterial region of an element, and/or as a coating on or in an element inhibiting the formation of biofilms and/or an antibacterial coating on or in an element which is introducible into or attachable on a human or animal body; wherein the glass and/or glass ceramic and/or ceramic material comprises: $SiO_2$ in a range from 60 to 75 wt %, and ZnO in a range from 1 to 7 wt %. In particular the element may be an element as described above.

Moreover, the invention relates to the use of a glass and/or glass ceramic and/or ceramic material for producing an element that is introducible into a human or animal body, in particular an element implantable into a human or animal body, or for producing an element attachable on a human or animal body. In a preferred embodiment, the invention relates to a glass and/or glass ceramic material as described above for producing implants, hermetic feedthroughs, vascular supports, in particular stents, catheters, artificial heart valves, casings for electronic devices such as transponders or entire defibrillators, pacemakers, and labs-on-chip, as well as contact lenses and/or coatings on contact lenses, wherein in the case of use as a contact lens and/or coating on contact lenses the content of coloring substances, e.g. iron oxide and other impurities should be selected as low as possible.

The use of the glass and/or glass ceramic and/or ceramic material according to the invention as a transponder material has proved to be particularly advantageous over known materials for this application. Transponder material is for instance employed for hermetic encapsulation of RFID transponders which are used for identification and tracking of domestic and farm animals, for example. The encapsulation with the described material allows for protection of the electronic component within the body, at the same time it protects the surrounding tissue from the electronics located in the interior of the encapsulation. It also provides protection from environmental influences such as moisture and dirt when the transponder is worn on the body. In this case, the inhibitory activity against biofilm formation of the material according to the invention proves also advantageous. This also applies to medical aids worn on the body such as contact lenses.

However, the transponders may as well be implanted, and in such an application the particularly good compatibility of the material according to the invention with human or animal cells is particularly favorable. This also applies to the use of the glass and/or glass ceramic and/or ceramic material of the invention as a casing or casing component for another electronic medical device, such as an active implant, as well as for applications as a material for medical aids that are introduced into the body, such as implants, vascular supports, in particular stents, and catheters, artificial heart valves, metering devices for active substances, and the like, and combinations of such items.

The element of the invention is suitable in conjunction with all medical devices or aids such as needles, suture materials, and staples, and the like, which are used on or in the body.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention will now be explained in more detail by way of exemplary embodiments and with reference to the accompanying drawings. Identical and similar components are designated with the same reference numerals, and features of the various exemplary embodiments can be combined and/or substituted by each other.

FIG. 8 shows cytotoxicity and hemocompatibility of soda-lime glass and several borosilicate glasses: representative images of cultured cells of MSSA, *Enterococcus faecalis, Enterococcus faecium, Escherichia coli, Klebsiella pneumonia, Pseudomonas aeruginosa, Proteus mirabilis, Staphylococcus epidermis;*

DETAILED DESCRITPION

Figure 1:
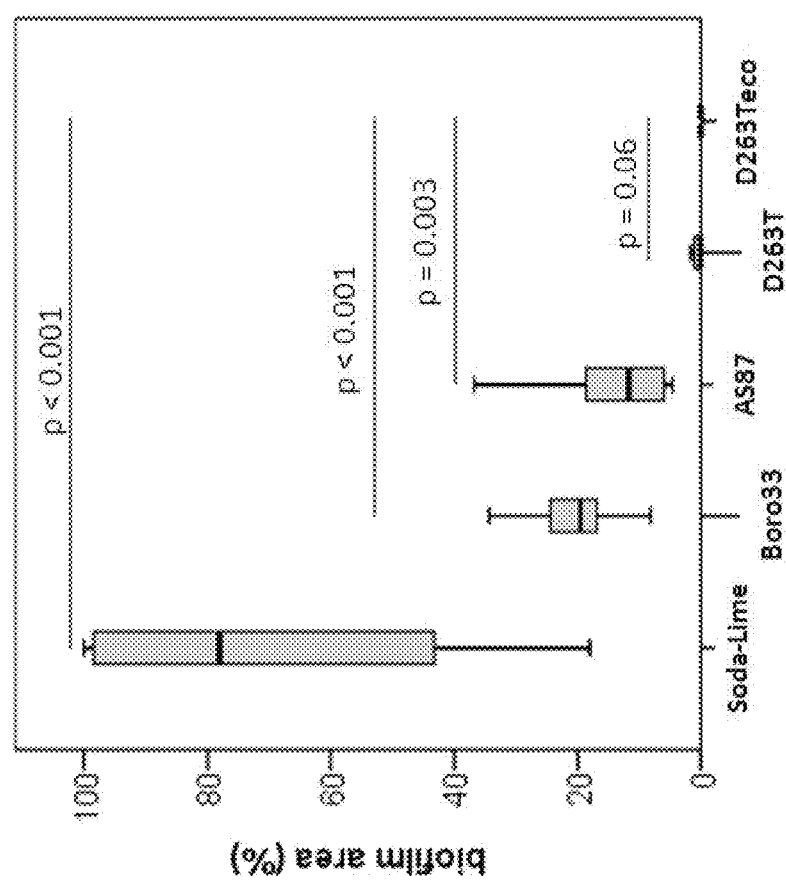
FIG. 1 shows an analysis and visualization of biofilm growth after culturing for 24 hours: initial data analysis of biofilm-covered surface, cumulatively for all bacteria.
Figure 2:
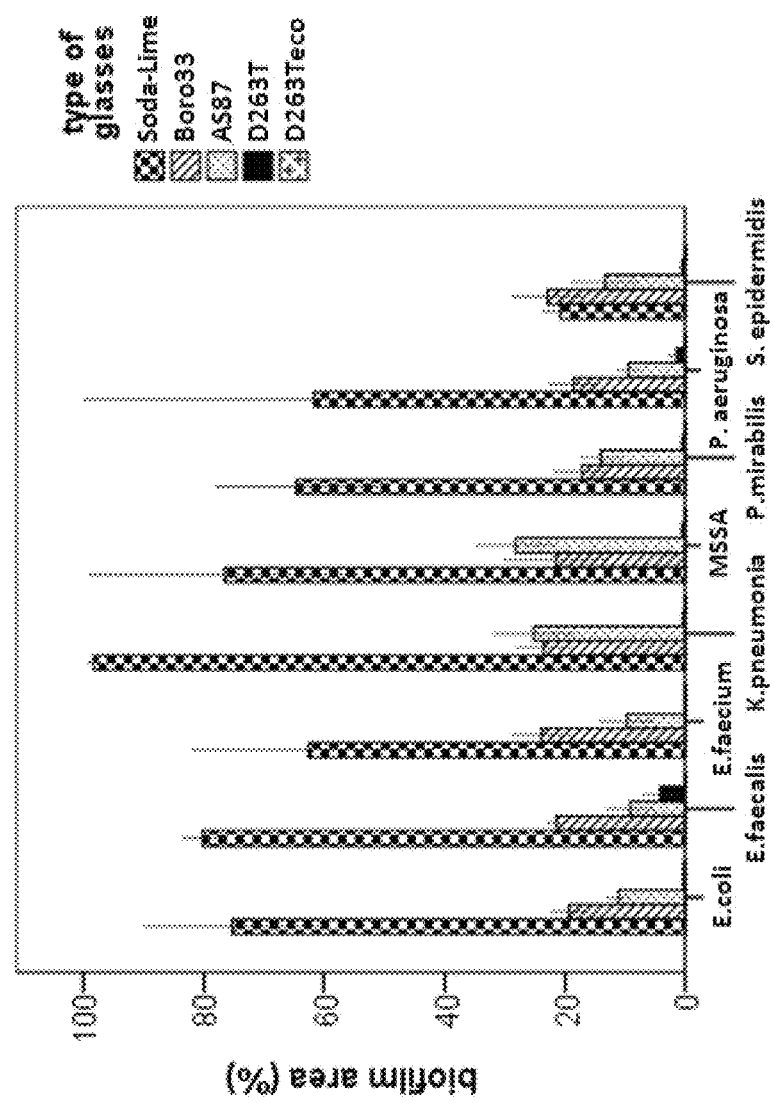
FIG. 2 shows an analysis and visualization of biofilm growth after culturing for 24 hours: quantitative analysis of biofilm-covered surface for each of the bacterial species.
Figure 3:
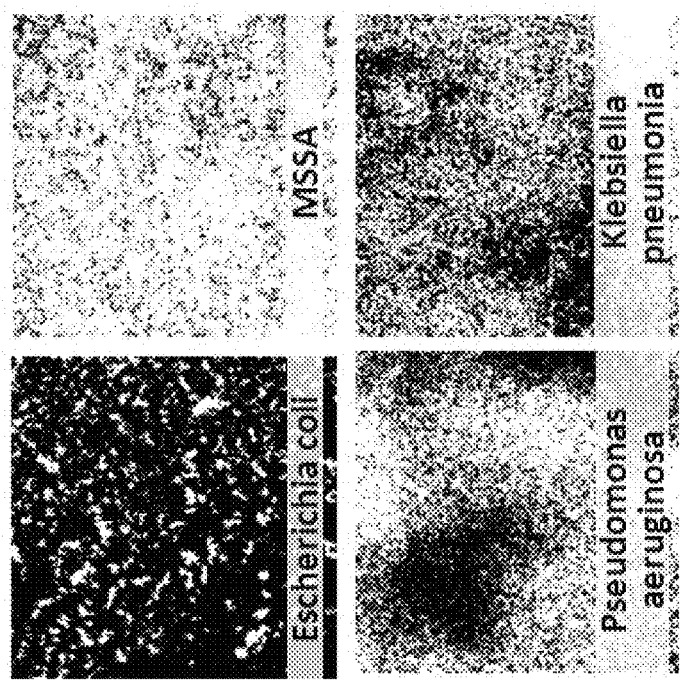
FIG. 3 shows an analysis and visualization of biofilm growth after culturing for 24 hours: representative images of biofilms on soda-lime glass.
Figure 4:
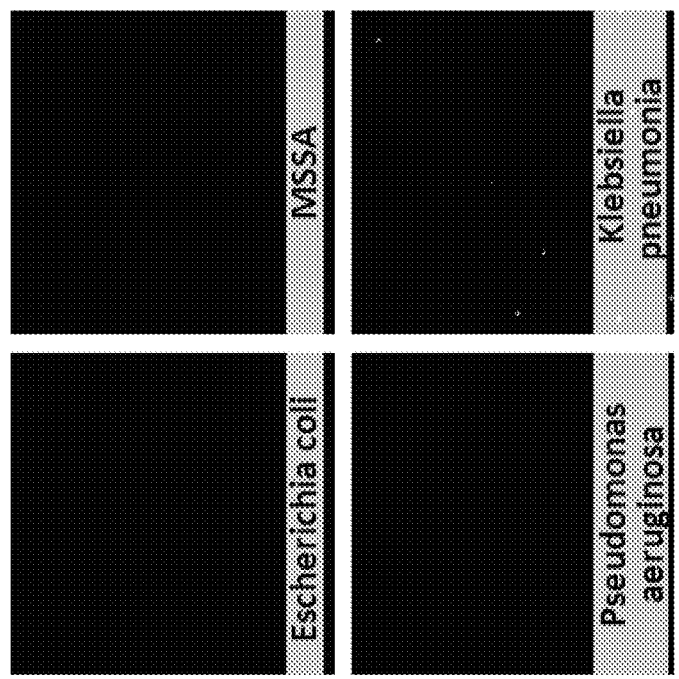
FIG. 4 shows an analysis and visualization of biofilm growth after culturing for 24 hours: representative images of biofilms on glass according to a first embodiment of the invention.
Figure 5:
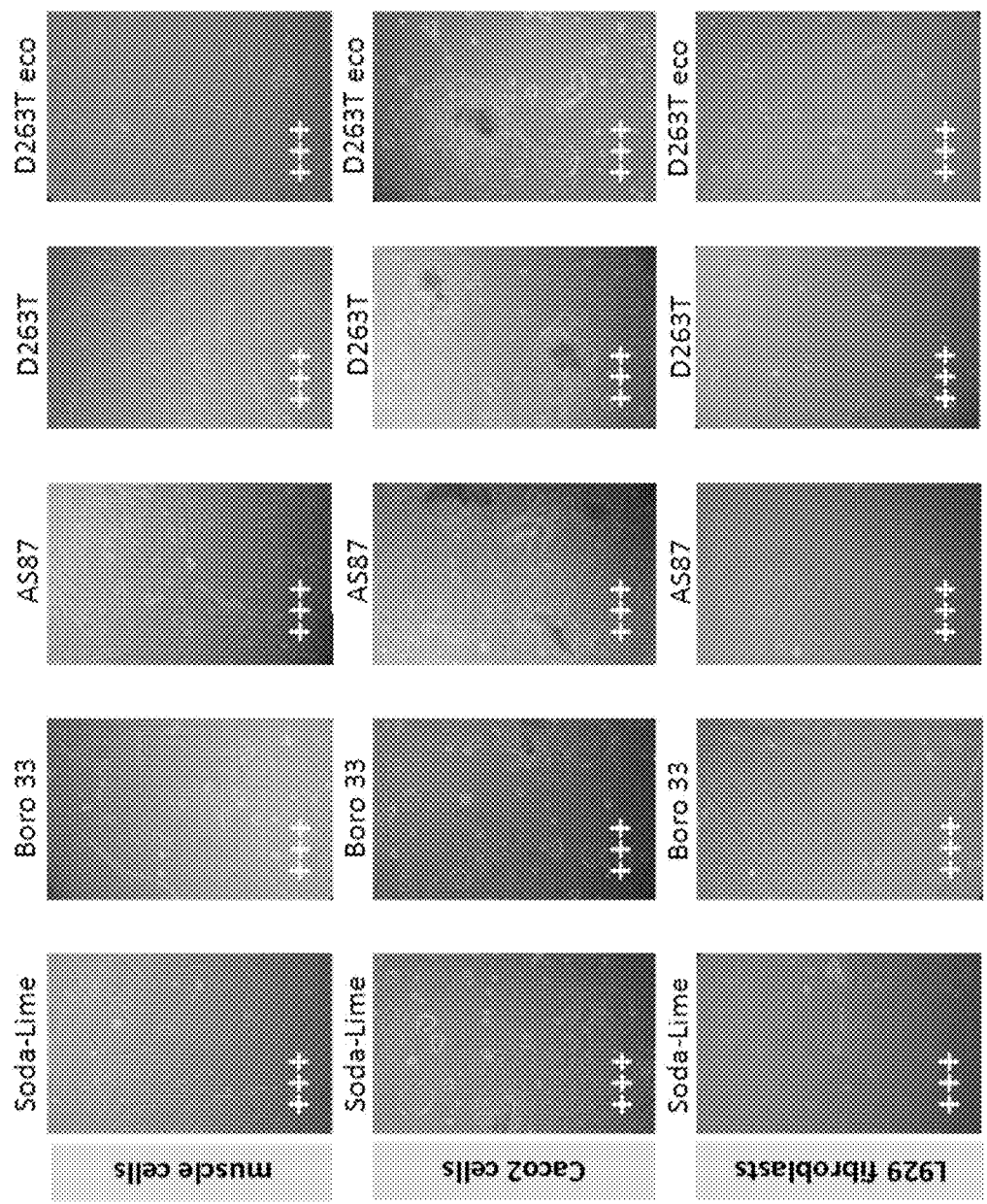
FIG. 5 shows cytotoxicity and hemocompatibility of soda-lime glass and several borosilicate glasses: representative images of cultured muscle cells, Caco2 cells, and L929 mouse cells.
Figure 6:
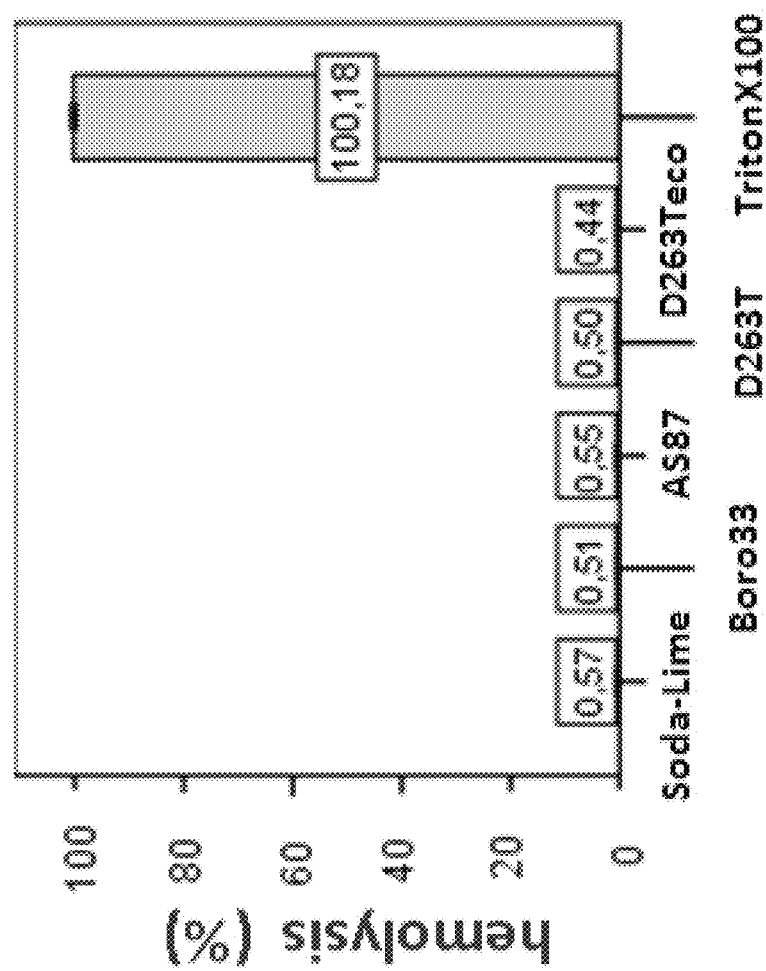
FIG. 6 shows cytotoxicity and hemocompatibility of soda-lime glass and several borosilicate glasses: data relating to hemolysis.

In order to investigate the inhibition of biofilm growth and the growth of human and animal cells, experiments were performed with different glasses. Glasses "BF1" and "BF2" were used as embodiments of the invention. Glasses "VG1", "VG2", and "VG3" were examined as comparative examples.

Table 1 below gives an overview of the chemical composition of the investigated glasses and glass ceramics:

| Content (wt %) | VG1 | VG2 | VG3 | BF1 | BF2 |
|---|---|---|---|---|---|
| $SiO_2$ | 72.48 | 81.19 | 61.59 | 63.03 | 63.06 |
| $Al_2O_3$ | 1.21 | 2.41 | 16.96 | 4.11 | 4.11 |
| $Na_2O$ | 14.36 | 3.52 | 12.32 | 6.08 | 6.08 |
| $K_2O$ | 1.21 | 0.08 | 4.14 | 8.51 | 8.51 |
| MgO | 4.32 | 0.00 | 3.94 | 0.00 | 0.00 |
| CaO | 6.43 | 0.00 | 0.00 | 0.00 | 0.00 |
| ZnO | 0.00 | 0.00 | 0.00 | 5.83 | 5.83 |
| $B_2O_3$ | 0.00 | 12.76 | 0.00 | 8.22 | 8.22 |
| $CeO_2$ | 0.00 | 0.00 | 0.30 | 0.00 | 0.00 |
| $TiO_2$ | 0.00 | 0.00 | 0.00 | 3.98 | 4.11 |
| $SnO_2$ | 0.00 | 0.00 | 0.40 | 0.00 | 0.00 |
| $Sb_2O_3$ | 0.00 | 0.00 | 0.00 | 0.20 | 0.00 |
| $F_2$ | 0.00 | 0.00 | 0.30 | 0.00 | 0.000 |
| FeO | 0.01 | 0.04 | 0.05 | 0.05 | 0.05 |
| $SeO_2$ | 0.00 | 0.00 | 0.00 | 0.00 | 0.03 |
| Total | 100.00 | 100.00 | 100.00 | 100.00 | 100.00 |

The glasses were tested in the form of sheets. Initially, the sheets were ultrasonically cleaned in 1% Deconex® 12 PA (Borer advanced cleaning solutions) at 40° C. for 15 min. The reagent was first removed with warm tap water and then by washing with deionized water. Thereafter, the sheets were treated using ultrasound in deionized water at 40° C. for 5 min. Finally, the sheets were dried in a nitrogen stream.

For the tests of biofilm formation, eight typical representatives of nosocomial infections were examined, namely MSSA: *Staphylococcus aureus*, methicillin-sensitive (ATCC 29213), *Staphylococcus epidermis* (Pp 62a), *Enterococcus faecalis* (ATCC 29212), *Enterococcus faecium* (SMZ 20477), *Escherichia coli* (ATCC 25922), *Klebsiella pneumonia* (ATCC 700603), *Pseudomonas aeruginosa* (PA01), and *Proteus Mirabilis* (VBK 4479).

The bacterial seed stocks were stored at −80° C. in 10 vol % glycerol solution. Prior to culturing in liquid medium, a strand of frozen bacteria was plated on lysogeny broth (LB) agar (1.5%) sheets and incubated overnight at 37° C. A single colony of each of the strains pathogenic for humans was cultured overnight in Mueller-Hinton (MH) medium at 37° C.

For biofilm formation, the cultures were freshly seeded in MH medium at a dilution of 1:1000 and were filled into 8×2 sections of silicone structures (SCHOTT Nexterion) attached to the glass sheets. Biofilms were grown at 37° C. over a period of 24 hours without shaking.

The biofilms were stained using the LIVE/DEAD BacLight Bacterial Viability Kit (Life Technologies). After staining, the bacterial supernatant was carefully removed, and the biofilms were carefully washed once with 300 μL (microliters) of a 0.9% NaCl solution. Then, they were embedded in Fluoromount-G (SouthernBiotech, BIOZOL) and covered with Nexterion® glass cover sheets (SCHOTT Nexterion). Visualization of the biofilms was performed as described above.

FIGS. 1 to 4 show results of the analysis and visualization of biofilm growth after culturing for 24 hours. The symbol p represents the p-value or significance value which is an indicator for the evaluation of statistical tests. In biological sciences, a threshold of 5% has been established (maximum error probability or significance level α=0.05). That means: If the probability for a result to be coincidental is less than 5%, it is considered to be "significant" (p<0.05).

The statistical analysis of the biofilm-covered surface areas (cumulative for all species) is given in Table 2 below, wherein N is the number of experiments, and SEM is "standard error of mean."

| Glass type | Biofilm surface area (%) | | Biofilm thickness (mm) | Degree of biofilm homogeneity (% incomplete) |
| --- | --- | --- | --- | --- |
| | Mean | SEM | | |
| VG1 (N = 24) | 69.33 | 7.041 | 10 to 30 | <10 |
| VG2 (N = 27) | 21.03 | 1.500 | 10 to 30 | <20 |
| VG3 (N = 25) | 14.32 | 1.875 | 10 to 30 | <50 |
| BF1 (N = 27) | 0.76 | 0.294 | 4 to 10 | >95 |
| BF2 (N = 25) | 0.07 | 0.026 | 4 to 10 | >95 |

All investigated human-pathogenic strains grew well on the surfaces of the glass corresponding to VG1 and on the sheets with the composition of VG2 and VG3. After 24 hours, most of the bacteria lived, which can be verified by green staining using SYTO9. The sporadic dead cells (stained red by propidium iodide) correspond to the usual decrease in biofilms.

On glasses BF1 and BF2 according to the invention, all investigated human-pathogenic germs showed reduced biofilm formation. Biofilm thickness is greatly reduced and is in a range between 4 μm and 10 μm (microns). In addition, the biofilms on the glasses of the invention exhibit morphological modifications with diffuse and porous structures. The surface areas actually covered by biofilms, namely 0.76±0.294% and 0.07±0.026% are greatly reduced in comparison to the other investigated glasses. Furthermore, the existing biofilms on the glasses of the invention exhibit greatly increased porosity of more than 95% in comparison to the other investigated glasses. Like the well grown biofilms on VG1, VG2, and VG3, the diminished biofilms only show a small number of dead cells.

These results surprisingly indicate that the chemical composition of the inventive materials BF1 and BF2 prevents the first step for adhesion of bacteria. So far, the investigated glasses according to the invention were used as resistant covers for touch panels of navigation devices integrated in automobiles, or as substrates for capacitive sensors and filters for camera modules in mobile phones, and as casing for CCD image sensors. Therefore, a person skilled in the field of microbiology never came into contact with these glasses.

FIGS. 5 to 8 illustrate results of in vitro determined cytotoxicity and hemocompatibility of soda-lime glass and different borosilicate glasses.

In order to evaluate modifications in cell morphology and growth performance, muscle cells, Caco2 cells, and L929 mouse fibroblasts were cultured on the different glasses for 48 hours. Compared with control cells in cell culture flasks, no changes in cell morphology and growth performance were found for all glasses. As can be seen from the images of FIG. 5, no apoptotic cells and abnormalities can be found in the cell environment. None of the examined glass compositions showed any signs of cytotoxicity.

For investigating hemolysis, erythrocytes were incubated on the glass surfaces for two hours. As proved by the results plotted in FIG. 6, none of the glasses exhibits proportions of hemolysis of more than 0.57%, regardless of the glass composition. According to the ASTM F756-00 standard, a hemoglobin release between 0 and 2% is considered non-hemolytic. This indicates that there is no detectable disorder of the membranes of the red blood cells.

Figure 7:
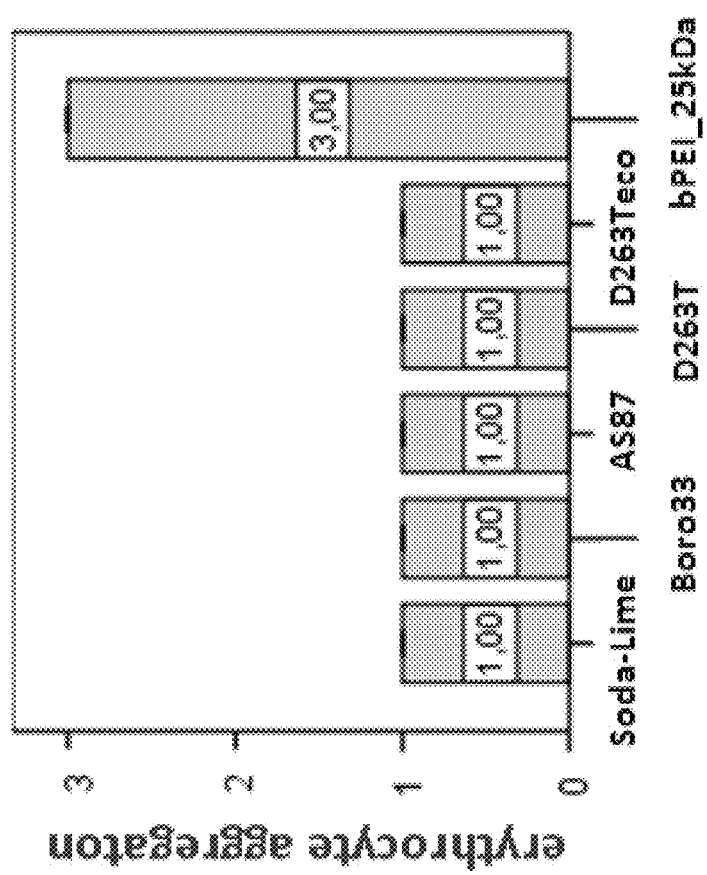
FIG. 7 shows cytotoxicity and hemocompatibility of soda-lime glass and several borosilicate glasses: data relating to erythrocyte aggregation.

Additionally it was investigated to what extent the types of material are capable of causing aggregation of erythrocytes. Aggregation of erythrocytes is an undesirable phenomenon which leads to side effects on the circulation and even lethal toxicity. The aggregation of erythrocytes was visualized microscopically after two hours of incubation on the glass surfaces. Treatment with 25 kDa bPEI at 30 mg/mL as a positive control resulted in the formation of aggregates (level 3 according to the classification discussed above). However, as shown in FIG. 7, no aggregation of red blood cells was found for any of the investigated materials. Moreover, all glass compositions exhibited very good hemocompatibility.

Among the germs used, S. epidermis basically showed low tendency to form biofilms on the glasses. By contrast, K. pneumoniae and MSSA showed an elevated tendency to adhesion and growth on the glass surfaces, as is illustrated by the images of FIG. 8. However, even for these germs biofilm formation is significantly reduced on the glasses of the invention.

Thus, glasses and/or glass ceramics and/or ceramics with the composition according to the invention are particularly suitable for the development of highly efficient anti-biofilm surfaces or coatings. Compared to the comparative examples VG1 to VG3, the glass and/or glass ceramic and/or ceramic material of the invention exhibits reduced biofilm adherence, increased biofilm porosity, and reduced biofilm thickness, and furthermore is excellently cytocompatible and hemocompatible without toxicity to eukaryotic cells.

With these surprising properties, diverse applications of the invention are possible in the field of medicine.

FIGS. 9a-9c and 10 illustrate exemplary applications for the glass or glass ceramic material of the invention.

Figure 9A:
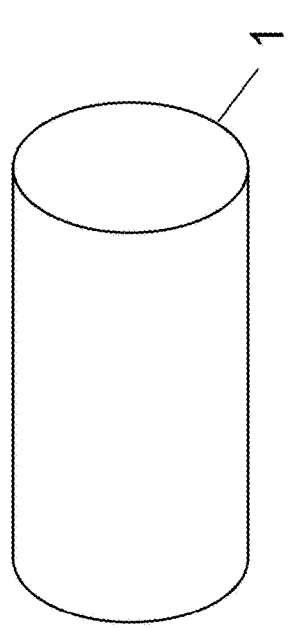
FIGS. 9a, 9b, and 9c schematically illustrate an implantable casing for an electronic component according to a first embodiment of the invention.
Figure 9B:
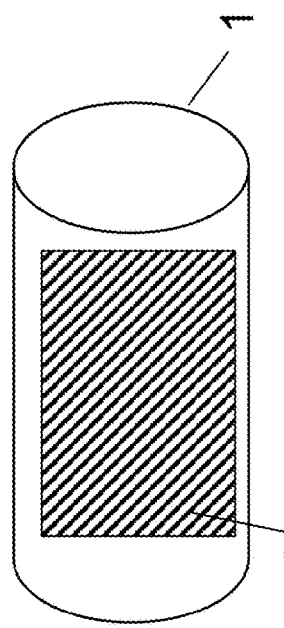
Figure 9C:
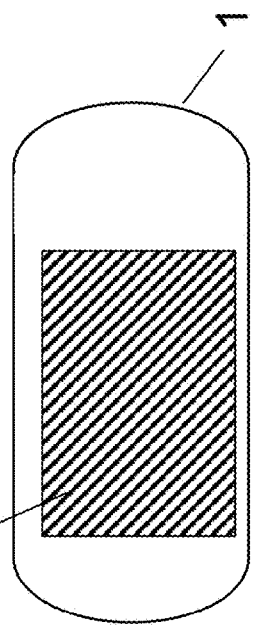

FIGS. 9a-9c illustrates a casing 1 for electronic components 2. Transponder casings, also known as transponders tubes, are easily manufactured as sections of tubing. One end is then sealed by fuse sealing, for example. Such a casing for a transponder is illustrated in FIG. 9A. An electronic component known as transponder is then introduced into the tube through the still open end shown on the right side in the figure, see FIG. 9B. The transponder may e.g. comprise an RFID chip or a sensor. The still open end of the tube may then be closed by heat application, for example using a laser and/or infrared radiation, so that the casing will then advantageously be hermetically sealed, as shown in FIG. 9C. In a preferred embodiment of the invention the casing is autoclavable.

The proportion of FeO in the glass and/or glass ceramic and/or ceramic material may promote the sealing of the tube in particular when a laser and/or infrared radiation is employed, in particular because it increases absorption of the material in the infrared spectral range.

Typical dimensions for such transponder casings are in a range of up to 10 mm, preferably in a range of up to 5 mm, more preferably in a range between 1 mm and 4 mm for the outer diameter, and in a range of up to 100 mm, preferably in a range of up to 70 mm, more preferably in a range between 5 mm and 50 mm in length. The wall thickness is in particular in a range of up to 2 mm, preferably in a range of up to 1.5 mm, more preferably in a range between 0.03 mm and 1.1 mm.

It is likewise possible for the element in the form of a tube section, for example, to be equipped with means permeable for an active substance, such as a membrane, on at least one end thereof, and to have an active substance deposited in the interior thereof. In this way, an implant for administering active substances can easily be produced.

It is also possible to integrate electronic components in such an implant for administering active substances, and the electronic component may in particular control the conditions of and/or trigger active substance release, in particular the timing and/or amount of active substance release. This electronic component may in particular as well be designed so as to be capable of communicating, via electrical conductors, e.g. wires and/or contacts, but also by wireless communication, with electronic devices outside the body which may in particular transmit control and/or sensor signals to the electronic component within the implant. In this way the described implant may be part of a more complex diagnostic and/or treatment apparatus.

It is similarly possible for substances, in particular liquids from the human or animal body to enter into the interior of the implant through the permeable means in order to be then analyzed there by the one or more electronic components. Data obtained from the analysis may be transmitted to electronic devices outside the human or animal body.

Figure 10:
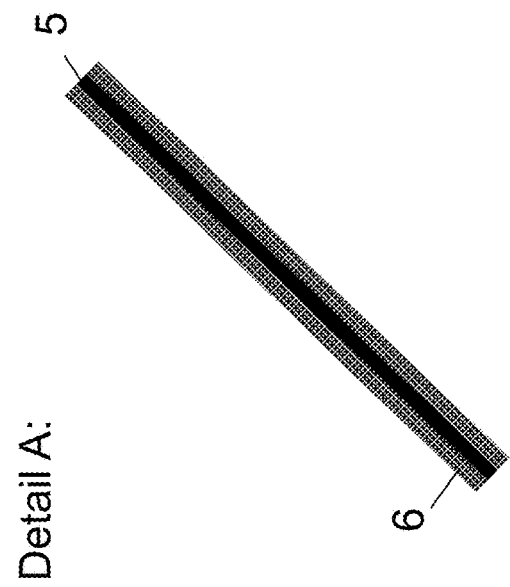
FIG. 10 schematically illustrates a vascular support according to another embodiment of the invention.
Figure 10:
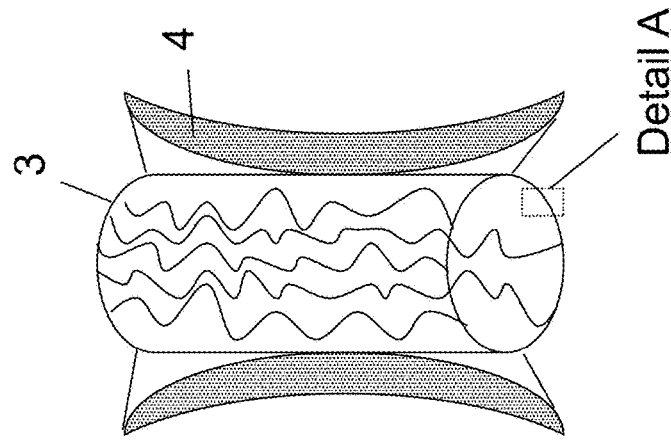

FIG. 10 illustrates a stent 3 as a further possible application of the glass or glass ceramic material according to the invention. Stent 3 is inserted in a hollow organ 4, for example a blood vessel. Stent 3 is made of a metal mesh, for example of titanium. The enlarged detail A on the right side of the figure shows a portion of a metal filament 5 of the metal mesh. According to the invention, metal filaments 5 have a coating 6, at least in areas thereof, which is made of the glass and/or glass ceramic material in accordance with a composition as described above. In this manner, susceptibility of the stent 3 for microbial colonization is significantly reduced as compared to known materials. Moreover, a stent coated in this manner is very well tolerated by the human or animal body.

It will be apparent to those skilled in the art that the invention is not limited to the examples described above, but rather may be varied in many ways. In particular it is possible for the features of the individual illustrated examples to be combined or substituted for each other.

What is claimed is:

1. A structural article, consisting of a unitary, monolithic material capable of inhibiting the formation of biofilms thereon when the structural article is in contact with a human or animal body, the material comprising a glass and/or glass ceramic and/or ceramic that comprises
    $SiO_2$ in a range from 60 to 75 wt %,
    $R_2O$ in a range from 5 to 20 wt %,
    RO in a range from 0 to 10 wt %,
    $Al_2O_3$ in a range from 1 to 6 wt %,
    $B_2O_3$ in a range from 0 to 10 wt %,
    $TiO_2$ in a range from 0 to 8 wt %,
    ZnO in a range from 1 to 7 wt %, and
    FeO in a range from 0 to 5 wt %,
    wherein $R_2O$ is an oxide or a combination of oxides selected from the group consisting of $Li_2O$, $Na_2O$, and $K_2O$, and
    wherein RO is an oxide or a combination of oxides selected from the group consisting of MgO, CaO, BaO, SrO, and any combinations thereof.

2. The structural article as claimed in claim 1, wherein the glass and/or glass ceramic and/or ceramic material comprises:
    $SiO_2$ in a range from 60 to 70 wt %,
    $R_2O$ in a range from 5 to 20 wt %,
    RO in a range from 0 to 10 wt %,
    $Al_2O_3$ in a range from 1 to 5 wt %,
    $B_2O_3$ in a range from 0 to 10 wt %,
    $TiO_2$ in a range from 0 to 8 wt %,
    ZnO in a range from 1 to 7 wt %,
    FeO in a range from 0 to 5 wt %, and
    $Na_2O$ in a range from 2 to 10 wt %, and/or
    $K_2O$ in a range from 3.5 to 10 wt %.

3. The structural article as claimed in claim 1, wherein the glass and/or glass ceramic and/or ceramic material comprises:
    a content of Ag of less than 0.3 wt %; and/or
    a content of $P_2O_5$ of less than 0.5 wt %; and/or
    a content of F of less than 1 wt %.

4. The structural article as claimed in claim 1, wherein the structural article is configured to be introduced into the human or animal body.

5. The structural article as claimed in claim 1, wherein the structural article is configured to be implanted into the human or animal body.

6. The structural article as claimed in claim 1, wherein the structural article is configured to be attached to the human or animal body.

7. The structural article as claimed in claim 1, wherein the structural article is selected from the group consisting of an implant, a casing feedthrough of an implant, a vascular support, a stent, a catheter, an artificial heart valve, a casing for a transponder, a casing for a defibrillator, a casing for a pacemaker, a lab-on-chip, and a contact lens.

8. The structural article of a material as claimed in claim 1, wherein the material comprises
    $SiO_2$ in a range from 62 to 66 wt %,
    $Al_2O_3$ in a range from 3.8 to 4.5 wt %,
    $B_2O_3$ in a range from 0 to 10 wt %,
    $TiO_2$ in a range from 3.5 to 4.5 wt %,
    ZnO in a range from 5 to 7 wt %,
    FeO in a range from 0.001 to 0.005 wt %,
    $Na_2O$ in a range from 5.9 to 6.5 wt %,
    $K_2O$ in a range from 8.3 to 9.1 wt %, and
    $SeO_2$ in a range from 0 to 0.04 wt %.

9. A structural article consisting of a substrate capable of inhibiting the formation of biofilms thereon when introduced into or attached onto a human or animal body, wherein the substrate includes a material of a glass and/or glass ceramic and/or ceramic of:
    $SiO_2$ in a range from 60 to 75 wt %,
    $R_2O$ in a range from 5 to 20 wt %,
    RO in a range from 0 to 10 wt %,
    $Al_2O_3$ in a range from 1 to 6 wt %,
    $B_2O_3$ in a range from 0 to 10 wt %,
    $TiO_2$ in a range from 0 to 8 wt %,
    ZnO in a range from 1 to 7 wt %, and
    FeO in a range from 0 to 5 wt %,
    wherein $R_2O$ is an oxide or a combination of oxides selected from the group consisting of $Li_2O$, $Na_2O$, and $K_2O$, and
    wherein RO is an oxide or a combination of oxides selected from the group consisting of MgO, CaO, BaO, SrO, and any combinations thereof.

10. The structural article as claimed in claim 9, wherein the glass and/or glass ceramic and/or ceramic material comprises:
    $SiO_2$ in a range from 60 to 70 wt %,
    $R_2O$ in a range from 5 to 20 wt %,
    RO in a range from 0 to 10 wt %,
    $Al_2O_3$ in a range from 1 to 5 wt %,
    $B_2O_3$ in a range from 0 to 10 wt %, TiO$_2$ in a range from 0 to 8 wt %,
ZnO in a range from 1 to 7 wt %,
FeO in a range from 0 to 5 wt %, and
Na$_2$O in a range from 2 to 10 wt %, and/or
K$_2$O in a range from 3.5 to 10 wt %.

11. The structural article as claimed in claim 9, wherein the glass and/or glass ceramic and/or ceramic material comprises:
a content of Ag of less than 0.3 wt %; and/or
a content of P$_2$O$_5$ of less than 0.5 wt %; and/or
a content of F of less than 1 wt %.

12. The structural article as claimed in claim 9, wherein the structural article is configured to be introduced into the human or animal body.

13. The structural article as claimed in claim 9, wherein the structural article is configured to be implanted into the human or animal body.

14. The structural article as claimed in claim 9, wherein the structural article is configured to be attached to the human or animal body.

15. The structural article as claimed in claim 9, wherein the structural article is selected from the group consisting of an implant, a casing feedthrough of an implant, a vascular support, a stent, a catheter, an artificial heart valve, a casing for a transponder, a casing for a defibrillator, a casing for a pacemaker, a lab-on-chip, and a contact lens.

16. The structural article of a material as claimed in claim 9, wherein the material comprises
SiO$_2$ in a range from 62 to 66 wt %,
Al$_2$O$_3$ in a range from 3.8 to 4.5 wt %,
B$_2$O$_3$ in a range from 0 to 10 wt %,
TiO$_2$ in a range from 3.5 to 4.5 wt %,
ZnO in a range from 5 to 7 wt %,
FeO in a range from 0.001 to 0.005 wt %,
Na$_2$O in a range from 5.9 to 6.5 wt %,
K$_2$O in a range from 8.3 to 9.1 wt %, and
SeO$_2$ in a range from 0 to 0.04 wt %.

* * * * *